United States Patent
Lu

(10) Patent No.: US 6,687,545 B1
(45) Date of Patent: Feb. 3, 2004

(54) CARDIAC STIMULATION SYSTEM AND METHOD FOR PERFORMING AUTOMATIC CAPTURE VERIFICATION DURING BIPOLAR STIMULATION

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 283 days.

(21) Appl. No.: 10/000,560

(22) Filed: Oct. 23, 2001

(51) Int. Cl.[7] .............................................. A61N 1/362
(52) U.S. Cl. ...................................................... 607/28
(58) Field of Search ................................ 607/28, 9, 27

(56) References Cited

U.S. PATENT DOCUMENTS

| | | | |
|---|---|---|---|
| 4,114,627 A | 9/1978 | Lewyn et al. | 607/13 |
| 4,502,492 A | 3/1985 | Bornzin | 607/121 |
| 4,549,548 A | 10/1985 | Wittkampf et al. | 607/27 |
| 4,991,583 A | 2/1991 | Silvian | 607/13 |
| 5,324,310 A | 6/1994 | Greeninger et al. | 607/28 |
| 5,431,693 A | 7/1995 | Schroeppel | 607/28 |
| 5,443,485 A | 8/1995 | Housworth et al. | 607/28 |
| 5,476,487 A | 12/1995 | Sholder | 607/28 |
| 5,683,447 A | 11/1997 | Bush et al. | 607/126 |
| 5,692,907 A | 12/1997 | Glassel et al. | 434/262 |
| 5,800,464 A * | 9/1998 | Kieval | 607/9 |
| 5,814,079 A * | 9/1998 | Kieval | 607/4 |
| 5,843,136 A | 12/1998 | Zhu et al. | 607/13 |
| 5,902,325 A | 5/1999 | Condic et al. | 607/28 |
| 5,935,158 A | 8/1999 | Holmstrom et al. | 607/116 |
| 5,991,656 A | 11/1999 | Olson et al. | 607/4 |
| 6,021,351 A | 2/2000 | Kadhiresan et al. | 607/19 |
| 6,044,298 A | 3/2000 | Salo et al. | 607/17 |
| 6,295,470 B1 * | 9/2001 | Mower | 607/14 |
| 6,341,235 B1 * | 1/2002 | Mower | 607/9 |
| 6,473,645 B1 * | 10/2002 | Levine | 607/9 |

OTHER PUBLICATIONS

Lu et al., The Occurrence of Anodal Stimulation During Bipolar Pacing in Implantable Pacemakers, IEEE, pp. 495–498 (1992).

* cited by examiner

Primary Examiner—Carl Layno

(57) ABSTRACT

An implantable cardiac stimulation device and method perform reliable, automatic capture verification during bipolar stimulation by eliminating capture verification during a cardiac cycle in which anodal stimulation is detected. Anodal stimulation is detected by the absence of a delay between the bipolar stimulation pulse and an evoked response sensed at the electrode functioning as the anode during stimulation. Automatic capture verification during bipolar stimulation is recommended only if anodal stimulation is not detected at a working stimulation output. During automatic capture verification, if anodal stimulation is detected, a capture threshold test is performed. A change in anodal stimulation threshold indicates a change in capture threshold. Thus, periodic anodal stimulation threshold tests are also performed to predict when a change in capture threshold has occurred. The device avoids adverse effects of anodal stimulation on evoked response detection and provides a method for predicting changes in capture threshold.

31 Claims, 7 Drawing Sheets

CARDIAC STIMULATION SYSTEM AND METHOD FOR PERFORMING AUTOMATIC CAPTURE VERIFICATION DURING BIPOLAR STIMULATION

FIELD OF THE INVENTION

The present invention relates generally to an implantable cardiac stimulation device. More specifically, the present invention is directed to an implantable cardiac stimulation device with automatic capture verification capabilities made possible during bipolar stimulation by monitoring for the presence of anodal stimulation.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave, and resulting atrial chamber contractions. The excitation pulse is further transmitted to, and through the ventricles via the atrioventricular (A-V) node and a ventricular conduction system, causing a depolarization known as an R-wave and resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired pacing output (amplitude and pulse width) and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-output pacing pulse was delivered to ensure capture. While this approach is straightforward, it quickly depletes battery charge and can result in patient discomfort due to extraneous stimulation of surrounding skeletal muscle tissue.

The capture "threshold" is defined as the lowest stimulation pulse output at which capture occurs. By stimulating the heart chambers at, or just above capture threshold, comfortable and effective cardiac stimulation is provided without unnecessary depletion of battery charge. Capture threshold, however, is extremely variable from patient-to-patient due to variations in electrode systems used, electrode positioning, physiological and anatomical variations of the heart itself, and so on. Furthermore, capture threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has indeed occurred. If a loss of capture is detected by such capture-verification algorithms, a threshold test is performed by the cardiac pacing device in order to re-determine the threshold and automatically adjust the stimulating pulse output. This approach, called "automatic capture", improves the cardiac stimulation device performance in at least two ways: 1) by verifying that the stimulation pulse delivered to the patient's heart has been effective, and 2) significantly increasing the device's battery longevity by conserving the battery charge used to generate stimulation pulses.

Commonly implemented techniques for verifying capture involve monitoring the intracardiac electrogram (EGM) signals received on the cardiac sensing electrodes. When a stimulation pulse is delivered to the heart, the EGM signals that are manifest concurrent with the depolarization of the myocardium are examined. When capture occurs, detection of an "evoked response," observed as the intracardiac P-wave or R-wave on the EGM, indicates contraction of the respective cardiac tissue. The depolarization of the heart tissue in response to the heart's natural pacemaking function is referred to as an "intrinsic response". Through sampling and signal processing algorithms, the presence of an evoked response following a stimulation pulse is determined. For example, if a stimulation pulse is applied to the ventricle, an R-wave sensed by ventricular sensing circuits of the pacemaker immediately following application of the ventricular stimulation pulse evidences capture of the ventricles.

If no evoked response is detected, typically a high-output back-up stimulation pulse is immediately delivered to the heart in order to provide backup support to the patient. An automatic threshold test is next invoked in order to re-determine the minimum pulse output required to capture the heart. An exemplary automatic threshold determination procedure is performed by first increasing the stimulation pulse output level to a relatively high predetermined testing level at which capture is certain to occur. Thereafter the output level is progressively decremented until capture is lost. The stimulation pulse output is then set to a level safely above the lowest output level at which capture was attained. Thus, reliable capture verification is of utmost importance in proper determination of the threshold.

Sensing an evoked response, however, can be difficult for several reasons. The greatest difficulty encountered is probably that of lead polarization. Lead polarization is commonly caused by electrochemical reactions that occur at the lead-tissue interface due to application of an electrical stimulation pulse across the interface. A lead-tissue interface is that point at which an electrode of the pacemaker lead contacts the cardiac tissue. If the evoked response is sensed through the same electrodes through which the stimulation pulses are delivered, the resulting polarization signal, also referred to as "afterpotential", formed at the electrode can corrupt the evoked response signal that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation output and other variables, many of which are continually changing overtime.

A false positive detection of an evoked response may lead to missed heartbeats, a highly undesirable and potentially life-threatening situation. Failure to detect an evoked response that has actually occurred will cause the pacemaker to unnecessarily invoke the threshold testing function in a chamber of the heart.

The importance of the problem of lead polarization is evident by the numerous approaches that have been proposed for overcoming this problem. For example, specially designed electrodes with properties that reduce the polarization effect have been proposed. When additional electrodes are available for sensing, polarization can be avoided by sensing the EGM signals using a different pair of electrodes than that used for stimulation.

Another problem that prevents reliable evoked response sensing during bipolar stimulation is the presence of anodal stimulation. Typically cathodal stimulation of the myocardium is recommended. Cathodal stimulation produces a negative pulse that acts to reduce the capacitance of the cell membrane allowing depolarization to occur. Anodal stimulation, that is a positive pulse, can also cause cell depolarization by first hyperpolarizing the cell and then, as the cell repolarizes, an overshoot causes depolarization. However, anodal stimulation generally requires higher stimulation output then cathodal stimulation, thus increasing the battery current drain. Anodal stimulation has been thought to increase the risk of arrhythmogenic depolarizations.

During bipolar stimulation, for example using a lead tip electrode as the cathode and a lead ring electrode as the anode, some degree of anodal stimulation may occur at the ring electrode. Anodal stimulation, when it occurs, has been found to change the bipolar evoked response signal morphology. The amplitude of the evoked response signal may be reduced, and the polarity may be reversed. Thus, signal processing algorithms used to recognize a bipolar evoked response signal for the verification of capture may fail to detect an evoked response signal altered due to anodal stimulation. During automatic capture verification, bipolar sensing is normally required to detect an evoked response. Therefore, unipolar stimulation may be required during automatic capture verification in order to reduce the interference of lead polarization and anodal stimulation with evoked response detection.

Bipolar stimulation, however, may be preferred over unipolar stimulation in many patients. Unipolar stimulation interferes with accurate arrhythmia detection in implantable cardioverter defibrillators. The requirement of unipolar stimulation in these devices has excluded the use of automatic capture verification capabilities. While problems of lead polarization can be overcome using low-polarization leads or special output or sensing circuitry, the problem of anodal stimulation preventing the use of automatic capture verification by evoked response detection during bipolar stimulation has not been fully addressed heretofore.

One approach to avoid the problem of lead polarization that would also avoid the problem of anodal stimulation is to detect evidence of the mechanical contraction of the heart chambers by measuring another physiological signal such as blood pressure, blood flow, heart wall motion, or changes in cardiac impedance. However, the use of additional physiological sensors adds cost, more complicated software and hardware requirements, additional implant time and increases reliability issues.

Since the stimulation output at which anodal stimulation begins to occur is generally higher than the cathodal capture threshold, anodal stimulation may not always occur during bipolar stimulation. However, it is a common practice to set stimulation output at a working margin above the cathodal capture threshold to allow for small fluctuations in threshold. Anodal stimulation may therefore occur at varying degrees during bipolar stimulation. Furthermore, the threshold at which anodal stimulation begins to occur is not a definitive value. The probability of anodal stimulation occurring increases with increasing stimulation amplitude.

One way to recognize when anodal stimulation is occurring is by examining the unipolar evoked response signal sensed using the anode electrode, typically a ring electrode, and device housing. When no anodal stimulation is present, a delay of 20 to 40 msec follows the bipolar stimulation pulse prior to the unipolar ring evoked response signal. This delay is thought to be due to the propagation time required for the depolarization wave front to travel from the cathodal stimulation site at the tip electrode to the sensing site at the ring electrode. In contrast, when anodal stimulation is present at the ring electrode, the evoked response immediately follows the stimulation pulse without any delay, and the evoked response signal is altered from the normal evoked response.

It would be desirable, therefore, to provide an implantable cardiac stimulation device capable of performing reliable capture verification during bipolar stimulation by determining when anodal stimulation is present and when it is not present. A method that allows capture detection during bipolar stimulation is needed, which overcomes the problem of anodal stimulation interfering with evoked response detection. Furthermore, it is desirable to implement a method for automatic capture detection during bipolar simulation in a cardiac stimulation device without requiring additional sensors or circuitry components that add cost, current drain and bulk to the system.

SUMMARY OF THE INVENTION

The present invention addresses this need by providing an implantable cardiac stimulation device and associated method for detecting when anodal stimulation is occurring during bipolar stimulation and eliminating capture verification based on evoked responses associated with anodal stimulation.

In one embodiment, a method and corresponding device are provided that monitor for anodal stimulation subsequent to a bipolar stimulation. If anodal stimulation is detected, the method and device ignore a detected response for purposes of capture verification. On the other hand, if anodal stimulation is not detected, the method and device perform capture verification based on the detected response.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing a method for detecting when anodal stimulation is present during bipolar stimulation with the goal of determining when automatic capture detection may be enabled during bipolar stimulation and when it should be disabled. A general cardiac stimulation device will thus be described in conjunction with FIGS. 1 and 2, in which the automatic capture detection features included in the present invention could be implemented. It is recognized, however, that numerous variations of such a device exist in which the methods of the present invention could be implemented without deviating from the scope of the present invention.

Figure 1:
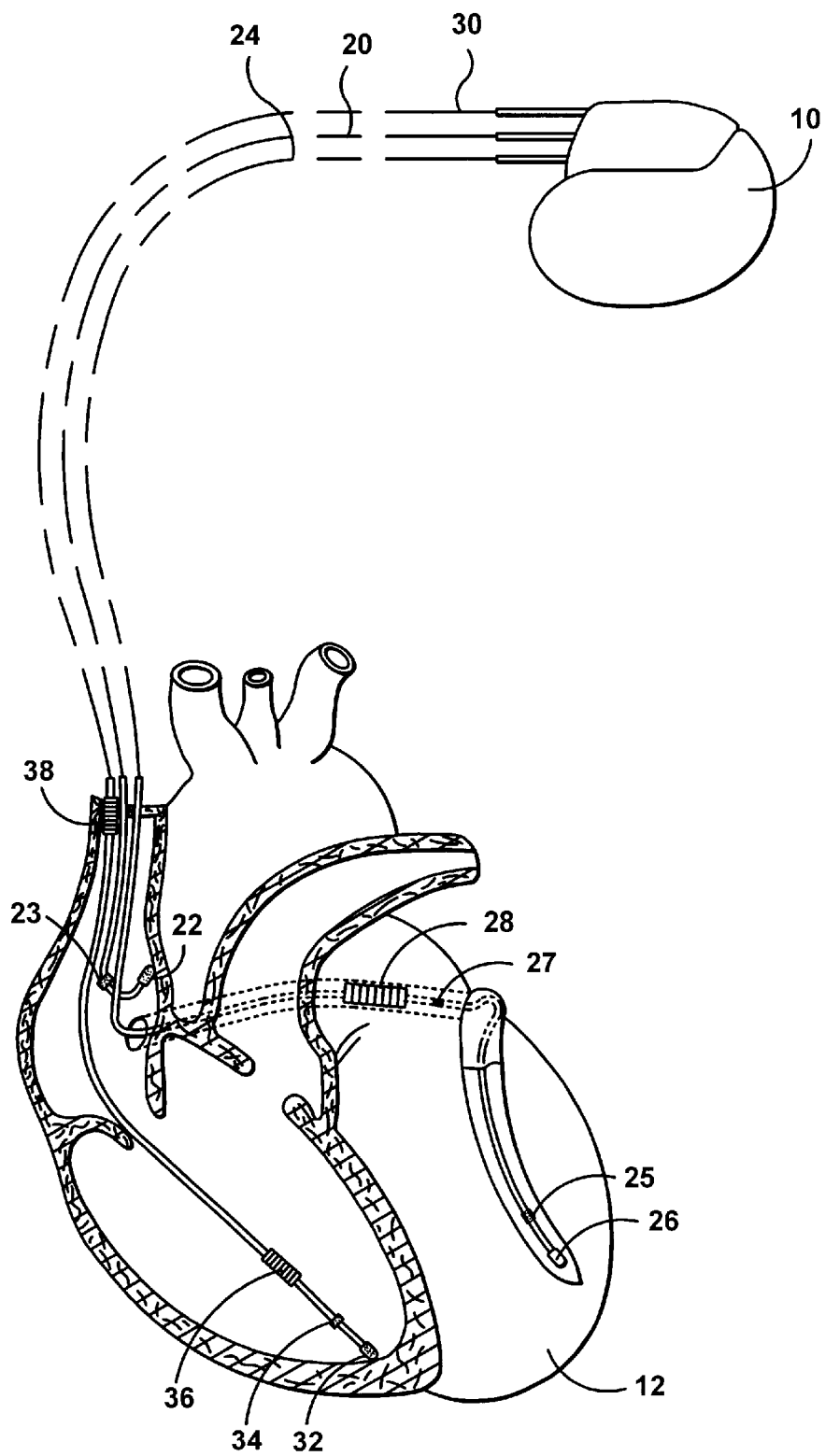
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a coronary sinus tip electrode 26 for unipolar stimulation or in combination with left ventricular ring electrode 25 for bipolar stimulation, left atrial pacing therapy using at least a coronary sinus ring electrode 27, and shocking therapy using at least a coronary sinus coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
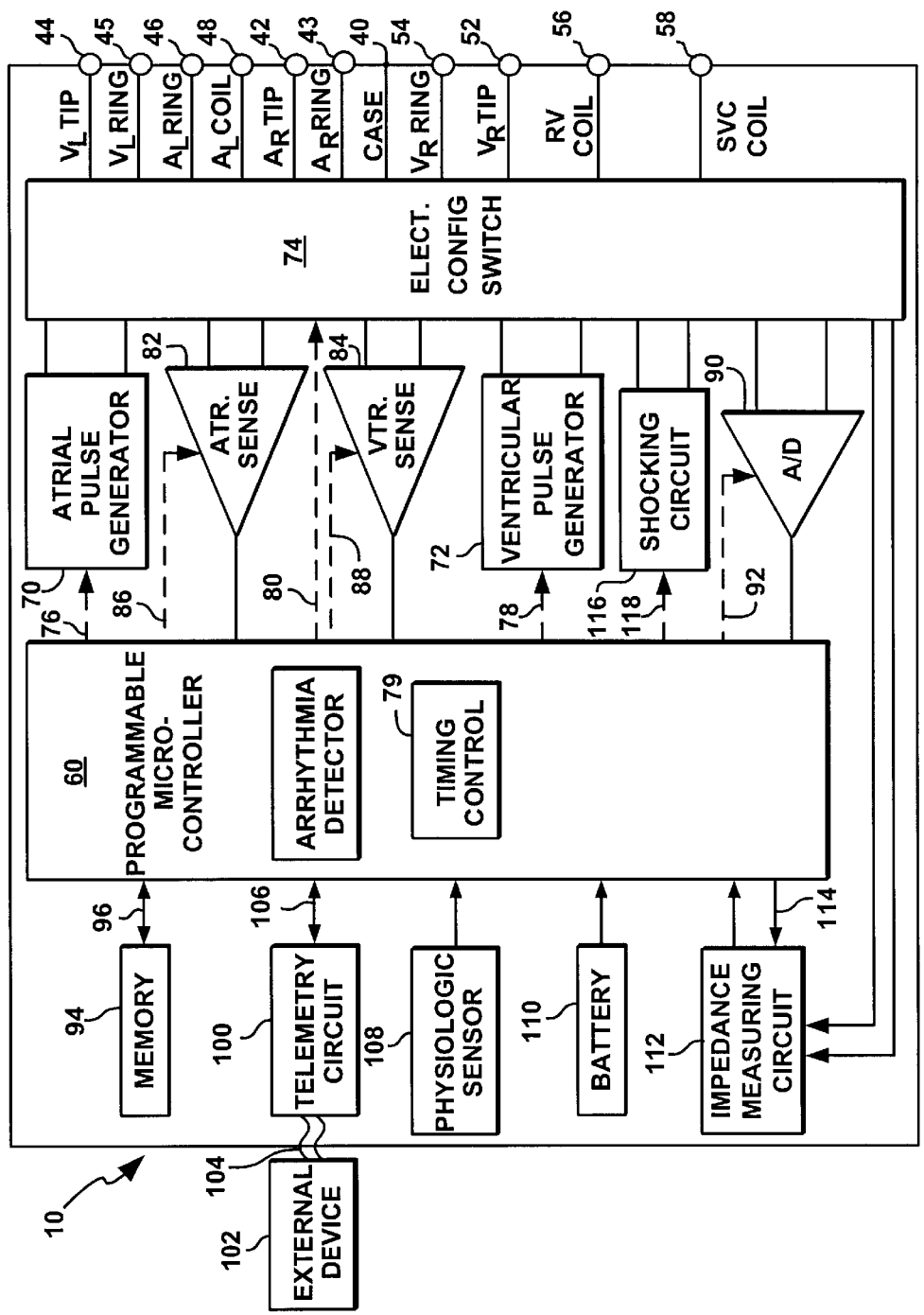
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The stimulation device 10 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the right atrial tip electrode 22. The connector may also include a right atrial ring terminal ($A_R$ RING) 43 for connection to the atrial ring electrode 23.

To achieve left chamber sensing, pacing, and shocking, the connector includes at least a coronary sinus tip terminal ($V_L$ TIP) 44, a coronary sinus ring terminal ($A_L$ RING) 46, and a coronary sinus shocking coil terminal (AL COIL) 48, which are adapted for connection to the coronary sinus tip electrode 26, the left ventricular ring electrode 25, the coronary sinus ring electrode 27, and the coronary sinus coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Stimulation during pacing can be performed in a bipolar mode in devices combining pacing and cardioversion/defibrillation functions because unipolar stimulation may interfere with arrhythmia detection. Hence, in one embodiment of the present invention, the switch bank 74 is configured such that: right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27.

Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. By employing the right ventricular coil electrode 36, possibly in combination with right ventricular ring electrode 34, the electrode surface during sensing is increased, advantageously reducing the effects of lead polarization.

In a preferred embodiment of the present invention, pacing therapy is delivered to one or more heart chambers through bipolar stimulation using a tip electrode, for example right atrial tip electrode 22, coronary sinus tip electrode 26 or right ventricular tip electrode 32, with the corresponding ring electrode, right atrial ring electrode 23, left ventricular ring electrode 25, and right ventricular ring electrode 34, respectively. Sensing of an evoked response following the bipolar stimulation pulse for the purposes of capture verification may be performed using either a bipolar or a unipolar electrode configuration in the same chamber that yields an adequate evoked response signal. However, in accordance with the present invention, unipolar sensing using the ring electrode, 23, 25 or 34, and the housing 40 is performed to determine if a bipolar stimulation pulse produced anodal stimulation at the ring electrode. Heretofore, undetected anodal stimulation would generally interfere with accurate capture detection during bipolar stimulation.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.), in order to determine the type of remedial therapy that is needed (e.g., bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". When automatic capture is enabled, the microcontroller 60 searches for a depolarization signal following a stimulation pulse during a "detection window" set by timing control circuitry 79 within microcontroller 60. The microcontroller 60 enables the data acquisition system 90 via control signal 92 to sample the cardiac signal that falls in the capture detection window. The sampled signal is evaluated to determine if it is an evoked response signal based on its amplitude, peak slope, or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to provide back-up support to the patient. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high energy level or the level at which capture is currently occurring) and decrease the energy level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 µA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected. As further illustrated in FIG. 2, the stimulation device 10 is shown to include an impedance measuring circuit 112, which is enabled by the microcontroller 60 by means of a control signal 114.

It is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
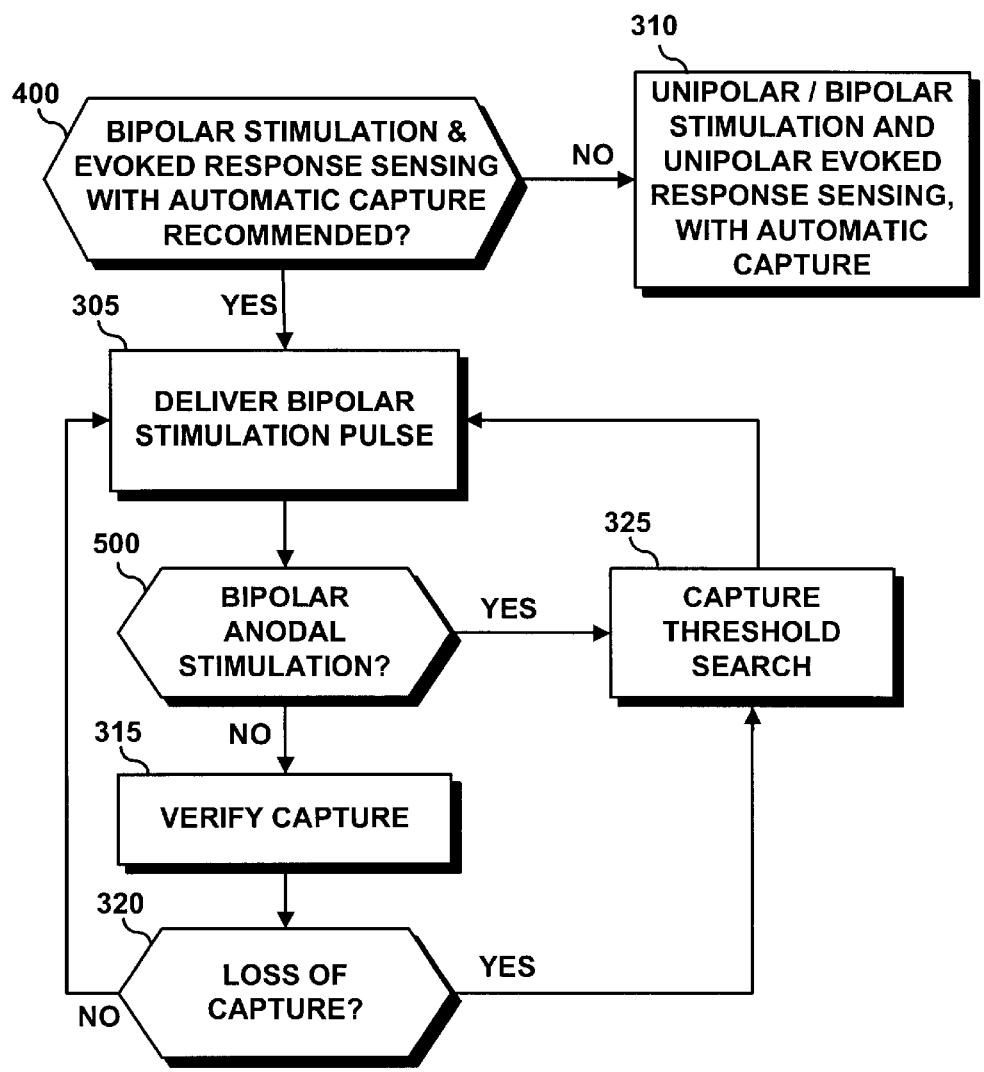
FIG. 3 is a flow chart providing an overview of the operations included in the present invention for performing automatic capture during bipolar stimulation.

In FIG. 3, a flow chart is shown describing an overview, as implemented in one embodiment of the device 10, of the operation and novel features provided by the present invention that allow the use of bipolar stimulation during automatic capture detection by detecting when anodal stimulation is present. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The methods and operations depicted in FIG. 3 may be applied in any chamber of the heart, atrial or ventricular. At step 400, a determination is made as to whether automatic capture detection may be recommended during bipolar stimulation and bipolar evoked response sensing. This determination is made during a test designed to determine if anodal stimulation occurs at a specified working output equal to the bipolar capture threshold plus a working margin. Details of the methods used in the determination made at step 400 will be described in detail in conjunction with FIG. 4.

If automatic capture detection can be recommended with bipolar stimulation, device 10 delivers bipolar stimulation pulses in conformance with the programmed operating mode at step 305. If bipolar stimulation during automatic capture detection is not recommended, the stimulation electrode configuration is set to unipolar at step 310 so that automatic capture may be enabled. Preferably, the clinician may selectively program the electrode configuration for stimulation and evoked response ("ER") sensing (unipolar or bipolar), and enable or disable automatic capture detection as desired.

At step 500, an anodal stimulation detection algorithm is executed following a bipolar stimulation pulse to determine if anodal stimulation is present. The methods for detecting anodal stimulation will be described in detail in conjunction with FIG. 5. If anodal stimulation is not present, the automatic capture detection algorithm can proceed with verifying capture in response to the bipolar stimulation pulse at step 315. Capture may be verified using any known or available capture verification techniques that reliably distinguish an evoked response from loss of capture, e.g., using the negative peak amplitude, peak slope, signal integral, or signal morphology matching.

If capture is verified, as determined at decision step 320, the device 10 continues delivering bipolar stimulation pulses at step 305 according to the programmed operating mode. If loss of capture is detected at decision step 320, a capture threshold search is performed at step 325. Typically, a sustained loss of capture, that is loss of capture detection on two or more consecutive primary stimulation pulses, is required before performing a capture threshold search. Safety back-up pulses are preferably delivered whenever loss of capture can be detected in accordance with known or available automatic capture algorithms.

If anodal stimulation is detected in an bipolar evoked response sensing configuration at step 500 following the bipolar stimulation pulse, the resulting evoked response is not used for capture verification at step 315. The evoked response signal is likely to be distorted by the effect of anodal stimulation, precluding accurate evoked response detection by the capture verification regime. The occurrence of anodal stimulation may also be indicative of a change in the bipolar capture threshold. If the stimulation output required to produce anodal stimulation has decreased, the bipolar capture threshold has also probably decreased. This early recognition of a possible decrease in capture threshold without performing a capture threshold search is not available in current automatic capture techniques and can be used advantageously to improve device longevity.

Therefore, if anodal stimulation is detected at step 500, a capture threshold search is performed at step 325 to re-determine the bipolar capture threshold. If the capture threshold has indeed decreased, the pulse output may be reduced to conserve battery charge and prevent anodal stimulation from interfering with capture verification during future heart cycles. The threshold search algorithm will automatically adjust the stimulating pulse output as necessary, after which device 10 returns to step 305 to continue delivering bipolar stimulation pulses at the adjusted pulse output.

Figure 4:
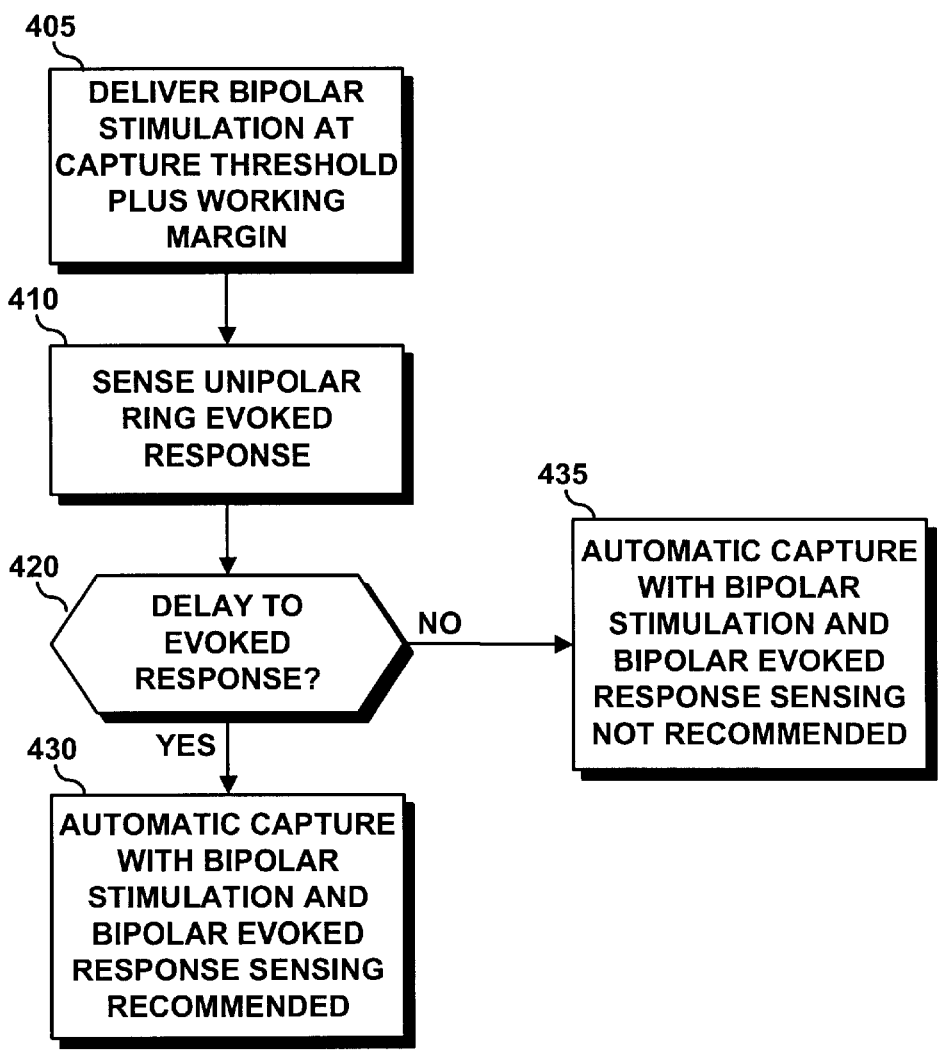
FIG. 4 is a flow chart depicting a method included in the present invention for determining if automatic capture detection can be used during bipolar stimulation according to the operations of FIG. 3.

FIG. 4 provides an overview of a method (or algorithm) performed at step 400 of FIG. 3 for determining if automatic capture verification can be recommended during bipolar stimulation. The method 400 may be performed under the supervision of a clinician observing EGM signals acquired by device 10 and displayed on external device 102. Preferably, the method 400 is performed automatically by device 10 with the final recommendation for automatic capture with bipolar stimulation displayed on the external device 102.

Prior to performing this method 400, a capture threshold search has been performed so that the bipolar capture threshold has been determined. The stimulation output is set equal to the known bipolar capture threshold plus a working margin, typically 0.25 Volts. At step 405, a bipolar stimulation pulse is delivered at this output level. At step 410, the unipolar evoked ring response signal is sensed using a ring electrode, such as right atrial ring electrode 23, right ventricular ring electrode 34, or left ventricular ring electrode 25.

For example, if the methods of FIGS. 3 and 4 are being applied in the right ventricle, the bipolar stimulation pulse is delivered between the right ventricular tip electrode 32 (cathode) and right ventricular ring electrode 34 (anode). Unipolar sensing for the detection of anodal stimulation is performed at step 410 using the right ventricular ring electrode 34 and an indifferent electrode, either the housing 40, the right ventricular coil electrode 36, or the SVC coil electrode 38. The unipolar sensing configuration for anodal stimulation detection is referred to hereafter as the "unipolar ring" configuration, regardless of whether the housing 40 or a coil electrode, 36 or 38, are used as the indifferent electrode.

This terminology presumes the common convention of bipolar stimulation being applied such that a tip electrode functions as the cathode and a ring electrode functions as the anode. The methods of the present invention may be applied in any bipolar stimulation configuration wherein unipolar sensing for the detection of anodal stimulation employs the electrode that functions as the anode during bipolar stimulation along with any suitable indifferent electrode.

In another example, if the methods of the present invention are being applied in the right atrium, the stimulation pulse at step 405 is delivered in a bipolar fashion between the right atrial tip electrode 22 (cathode) and right atrial ring electrode 23 (anode). The unipolar ring signal is then obtained by sensing at step 410 between the right atrial ring electrode 23 and the housing 40.

The unipolar ring signal is sampled at step 410 for a predetermined time beginning just after the bipolar stimulation pulse such that the evoked response signal may be acquired. At step 420, the time from the stimulation pulse to the evoked response is determined. Preferably, the time from the stimulation pulse to the onset of the evoked response is determined. Alternatively, the time from the stimulation pulse to the peak amplitude, peak slope, or another predetermined evoked response signal characteristic, may be measured. Typically, a 20 to 40 ms conduction delay to the unipolar ring evoked response signal occurs when only cathodal stimulation is present.

Therefore, if there is a delay to the evoked response as determined at decision step 420, then anodal stimulation is not indicated and will not interfere with evoked response detection during bipolar evoked response sensing of the bipolar stimulation at the currently programmed output. Automatic capture detection may be recommended with bipolar stimulation and bipolar evoked response sensing at step 430 and device 10 proceeds to step 305 of FIG. 3 to deliver bipolar stimulation and perform automatic capture verification.

If no delay to the evoked response is measured at step 420, then anodal stimulation is occurring at the ring electrode at the programmed stimulation output. This anodal stimulation will likely interfere with accurate evoked response detection during automatic capture detection. Therefore, at step 435, automatic capture detection during bipolar stimulation and bipolar evoked response sensing is not recommended. In other terms, evoked response sensing cannot be carried out in a bipolar configuration. A message indicating such is preferably displayed on external device 102. Device 10 proceeds to step 310 shown in FIG. 3 to automatically program unipolar stimulation.

Figure 5:
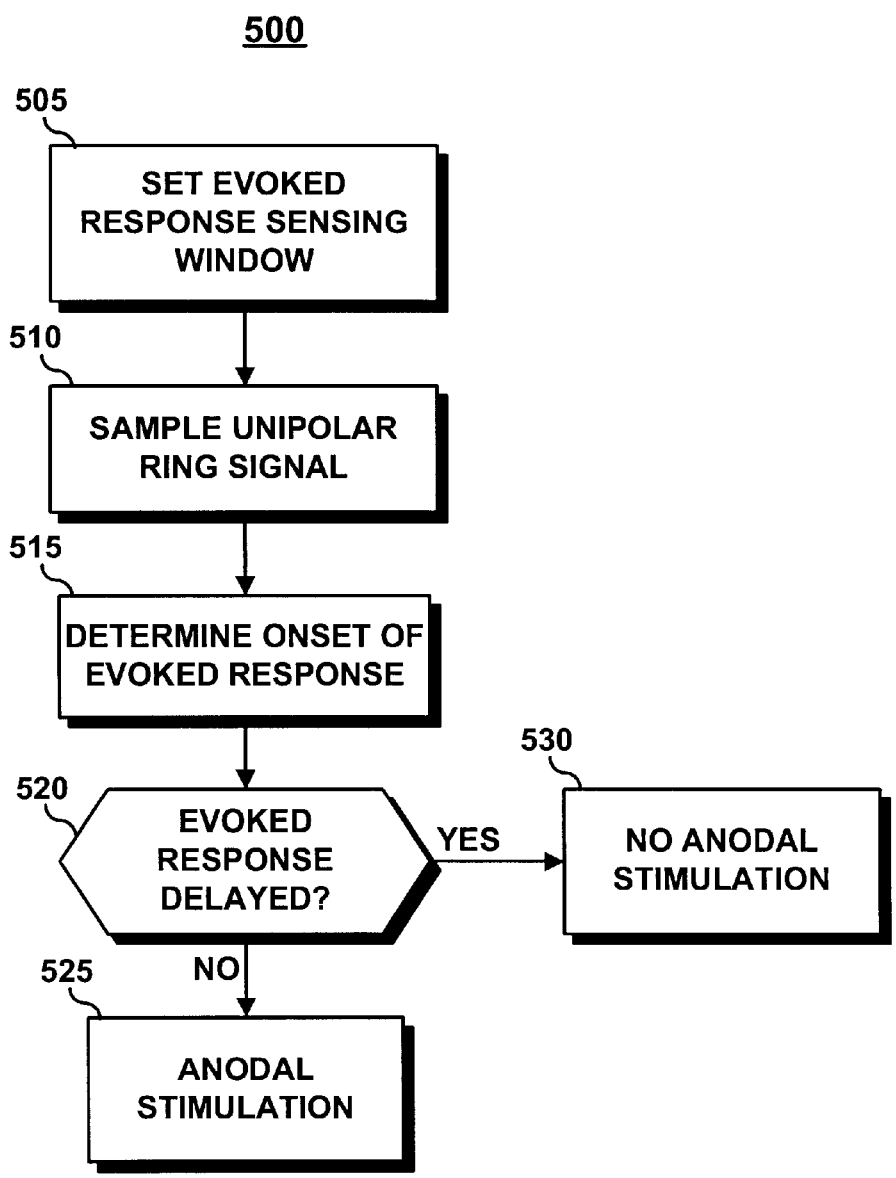
FIG. 5 is a flow chart depicting a method included in the present invention for determining if anodal stimulation has occurred with the delivery of a bipolar stimulation pulse during the automatic capture operations of FIG. 3.

FIG. 5 provides an overview of the methods used at step 500 of FIG. 3 for determining if anodal stimulation is occurring during the delivery of bipolar stimulation. At step 505, an evoked response sensing window is set following the bipolar stimulation pulse delivered at step 305 of FIG. 3. The evoked response sensing window begins shortly after the stimulation pulse and extends a predetermined time during which the evoked response is expected to occur. At step 510, the unipolar ring signal is sampled. At step 515, microcontroller 60 determines the time of the onset of the evoked response from the sampled unipolar ring signal.

If the onset of the evoked response occurs after a delay, typically 20 to 40 ms following the stimulation pulse, as determined at decision step 520, then anodal stimulation is not occurring as concluded at step 530. If there is no delay to the evoked response, then anodal stimulation is present as concluded at step 525. The result of anodal stimulation 525 or no anodal stimulation 530 is used by microcontroller 60 in determining how to proceed in the methods shown in FIG. 3.

In a preferred embodiment, periodic tests are also performed to determine the threshold for anodal stimulation. The threshold for anodal stimulation is defined as the lowest stimulation output at which anodal stimulation occurs and should not be confused with the capture threshold required to depolarize the cardiac tissue. If the anodal stimulation threshold has increased or decreased, the capture threshold has also likely increased or decreased. Therefore, if a periodic anodal stimulation threshold test reveals a decrease in anodal stimulation threshold, then a capture threshold search is warranted. In this way, a decrease in capture threshold can be recognized prior to performing an actual capture threshold search. Furthermore, early recognition of a decrease in capture threshold, which allows a downward adjustment in stimulation output, improves the battery charge savings offered by automatic capture detection methods.

Figure 6:
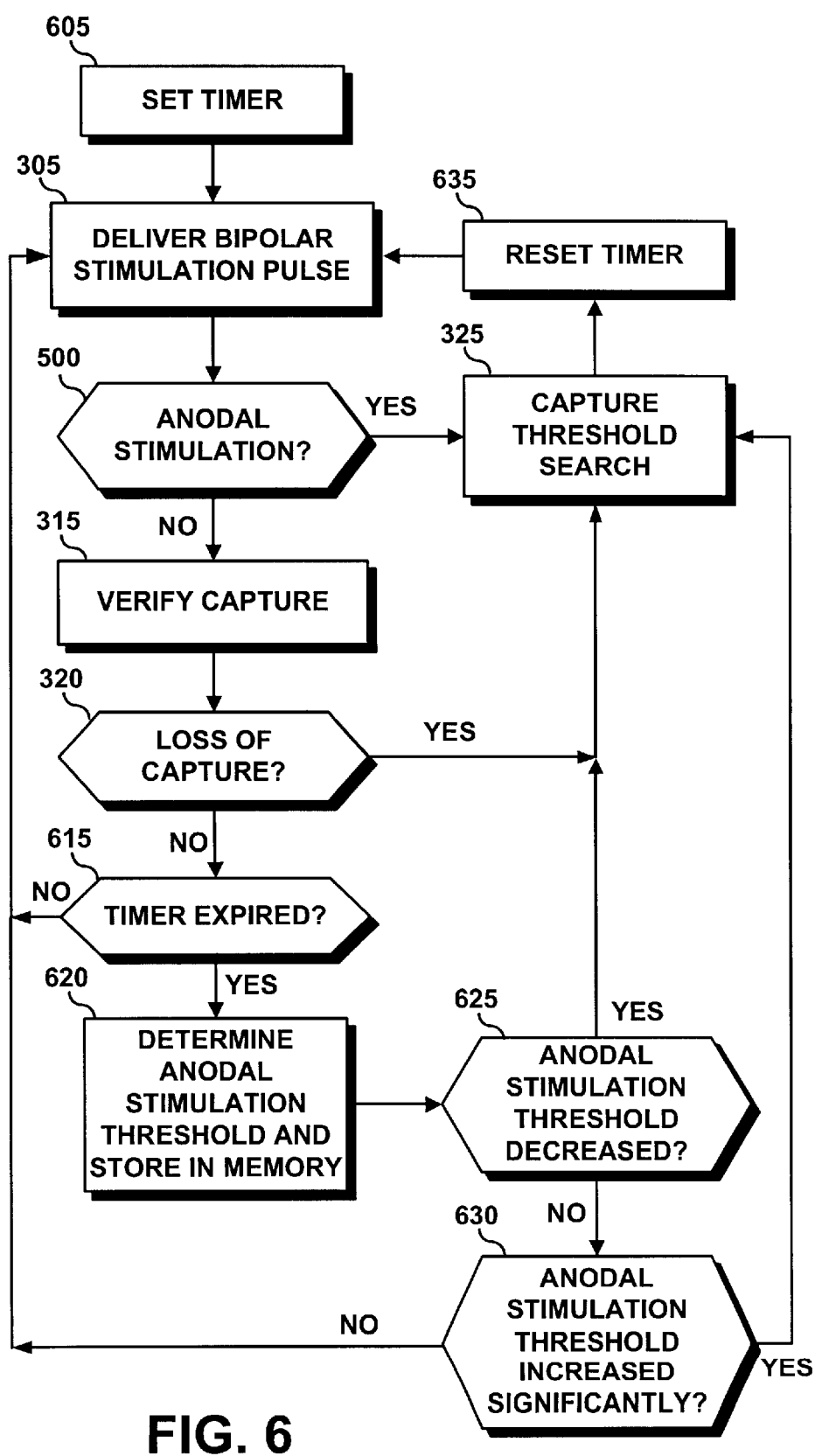
FIG. 6 is a flow chart depicting a method for determining if a change in capture threshold has occurred, warranting a threshold search to be performed, during the automatic capture operations of FIG. 3.

FIG. 6 illustrates how a periodic anodal stimulation threshold test may be implemented in one embodiment of the present invention. At step 605, a timer is set which will determine the frequency of anodal stimulation threshold testing. Preferably the timer interval is programmable and may be set according to patient need, such as every six hours. Alternatively, the timer may be a counter set in terms of a number of sensed or stimulated cardiac events.

At step 305, device 10 is operating in a bipolar stimulation mode with automatic capture detection enabled. Bipolar stimulation pulses are delivered in conformance with the programmed operating mode. Whenever a bipolar stimulation pulse is delivered, the anodal stimulation detection algorithm 500 is performed as previously described in conjunction with FIG. 5. If anodal stimulation is detected, a capture threshold search is performed at step 325 to adjust the pulse output. At step 635 the anodal stimulation threshold test timer is reset, and device 10 returns to the normal operating mode at step 305.

If anodal stimulation is not detected at step 500, capture verification is performed at step 315. If a sustained loss of capture is detected at decision step 320, a capture threshold search is performed at step 325. The anodal stimulation threshold test timer is reset at step 635, and device 10 returns to the normal operating mode at step 305.

Thus, the timer is reset whenever the stimulation output is automatically adjusted as the result of a capture threshold test. When a capture threshold test has been performed, it is unnecessary to determine the anodal stimulation threshold in order to detect a possible change in capture threshold. If no loss of capture is detected at step 320, however, the microcontroller 60 determines if the timer has expired at step 615. If the timer has not expired, device 10 continues to operate in the normal mode by returning to step 305.

If the timer has expired, the stimulation will have been delivered at the same output for the entire timer interval without a detected loss of capture. After delivering bipolar stimulation at the same output level for the predetermined interval of time, it is desirable to re-determine the anodal stimulation threshold in case there has been a decrease in capture threshold that warrants an adjustment of stimulation output. Thus, an anodal stimulation threshold test is performed at step 620 and the result is stored in memory 94. A preferred method for determining the anodal stimulation threshold will be described in conjunction with FIG. 7.

Once the anodal stimulation threshold is determined, it is compared to the last known anodal stimulation threshold at step 625. If the anodal stimulation threshold has decreased, a capture threshold search is performed at step 325. If anodal stimulation threshold has decreased, the bipolar capture threshold has also likely decreased, permitting a decrease in stimulation output.

A threshold search will also be performed at step 325 if the anodal stimulation threshold has increased by more than a predetermined amount, as determined at decision step 630. A small increase in capture threshold may not yet have caused a loss of capture, but the working margin may have become insufficient to reliably avoid loss of capture. Therefore it is desirable to perform a capture threshold search to adjust the pulse output appropriately. If the anodal stimulation threshold has not changed, device 10 returns to the normal operating mode at step 305.

Figure 7:
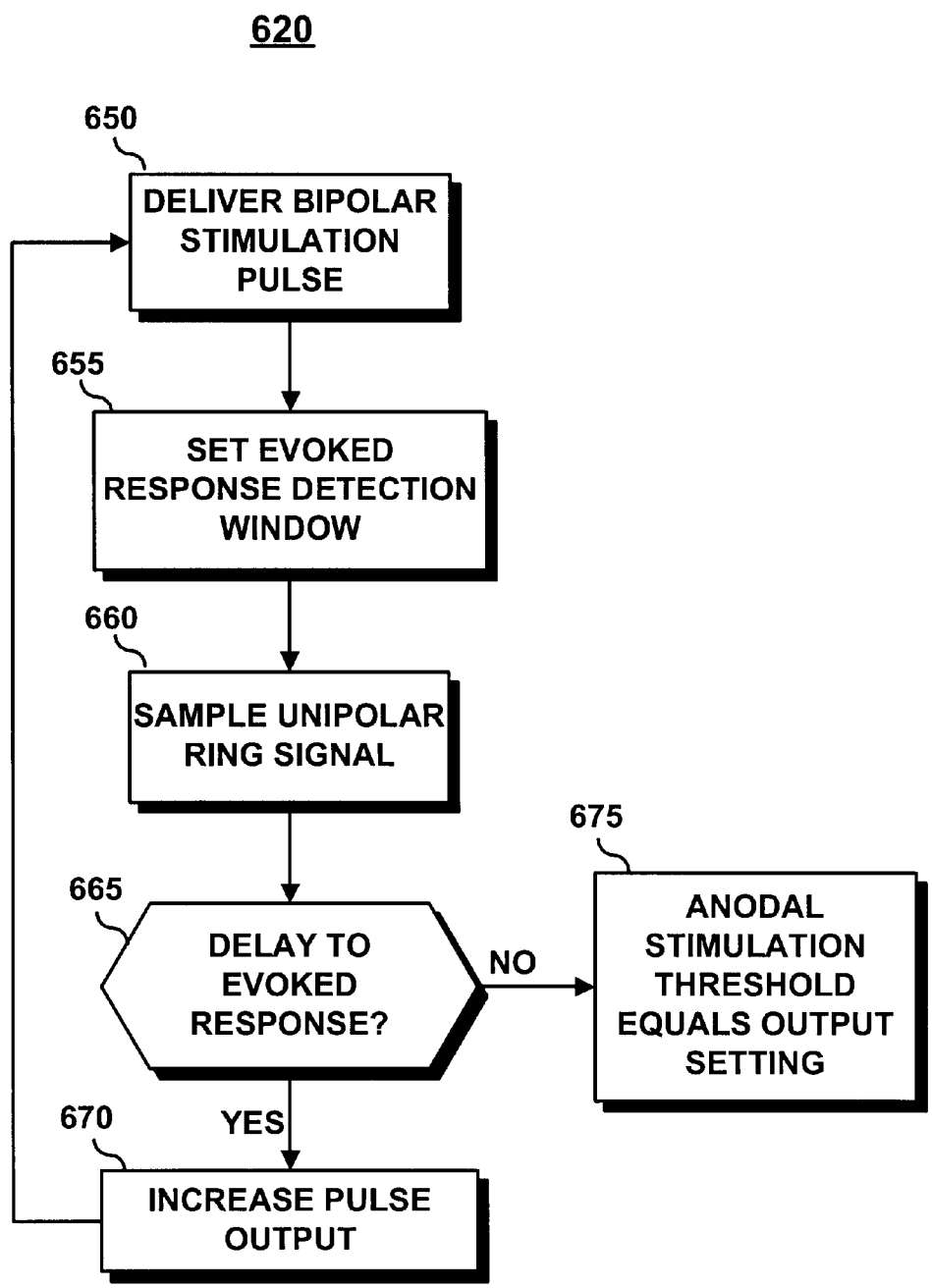
FIG. 7 is a flow chart depicting a method for determining the anodal stimulation threshold to be performed during the operations of FIG. 6.

In FIG. 7, a preferred method for determining the anodal stimulation threshold at step 620 of FIG. 6 is shown. At step 650, a bipolar stimulation pulse is delivered. This pulse is delivered at the existing, working pulse output setting. Since this setting has been active during the operation of automatic capture and anodal stimulation detection, no anodal stimulation is expected to occur. An evoked response detection window is set at step 655. The unipolar ring evoked response signal is sampled during the evoked response window at step 660. If a delay to the onset of the evoked response is detected, as determined at decision step 665, then anodal stimulation is not present. This is the result expected for the first test setting at the working output.

The stimulation output is then increased at step 670 by a pre-determined interval in pulse amplitude or pulse width. The method 620 then returns to step 650 to deliver another bipolar stimulation pulse at the incremented pulse output.

This process, steps 650 through 670, is repeated until a delay to the unipolar ring evoked response is not detected at step 665, indicating the presence of anodal stimulation. Thereafter, the lowest output setting at which anodal stimulation was first detected is stored in memory 94, at step 675 as the anodal stimulation threshold.

Alternatively, anodal stimulation threshold could be determined by first setting the stimulation output to a high level, e.g., the last known anodal stimulation threshold, and then decreasing the stimulation output until no anodal stimulation is detected. If anodal stimulation is not detected at the first test setting, then the stimulation output is increased until anodal stimulation is detected. The lowest output at which anodal stimulation is detected is the anodal stimulation threshold. Numerous algorithms for varying the bipolar stimulation pulse output until the anodal stimulation threshold is identified may be successfully applied without deviating from the scope of the present invention.

Thus, a cardiac stimulation system and method have been described that allow the use of bipolar stimulation and bipolar evoked response sensing during automatic capture verification by detecting when anodal stimulation is present. Detection of anodal stimulation prevents the distorted evoked response signal associated with anodal stimulation from being inappropriately detected as a loss of capture by automatic capture detection regimes.

Furthermore, detection of anodal stimulation or a change in anodal stimulation threshold is used in the present invention as an indicator of change in capture threshold. A change in capture threshold can be recognized before a capture threshold search is performed by monitoring anodal stimulation threshold. Capture threshold searches need only be performed when a change in capture threshold is indicated by a change in anodal stimulation threshold. In this way, changes in capture threshold may be recognized more quickly, using less battery charge, than by traditional periodic capture threshold tests.

Early detection of a rise in capture threshold reduces the likelihood of loss of capture, precluding the need for high-energy back-up pulses. Monitoring anodal stimulation threshold will generally use less battery charge than a capture threshold search that typically requires back-up safety pulses.

Thus, the present invention further improves the battery longevity benefit of automatic capture by allowing the prompt reduction of stimulation output in response to reduced capture threshold and foreseeing a rise in capture threshold before loss of capture has occurred. The present invention may be implemented without adding complex or bulky circuitry components or additional sensing electrodes.

While detailed descriptions of specific embodiments of the present invention have been provided, it would be apparent to those reasonably skilled in the art that numerous variations to the described algorithms are possible in which the concepts and methods of the present invention may readily be applied. The descriptions provided herein, therefore, are for the sake of illustration and are no way intended to be exclusive.

What is claimed is:

1. In a cardiac stimulation device, a method of performing automatic capture verification in a cardiac chamber during bipolar stimulation, the method comprising:
    monitoring for anodal stimulation subsequent to a bipolar stimulation;
    if anodal stimulation is detected, ignoring a detected response for purposes of capture verification; and
    performing capture verification based on the detected response if anodal stimulation is not detected.

2. The method of claim 1, wherein detecting anodal stimulation comprises sensing a unipolar evoked ring response signal from an electrode functioning as an anode during bipolar stimulation.

3. The method of claim 2, further including:
    setting an evoked response detection window following the delivery of a bipolar stimulation pulse; and
    sampling the unipolar evoked ring response signal during the evoked response detection window.

4. The method of claim 3, further including measuring a delay interval between a bipolar stimulation pulse and a predefined characteristic of a unipolar evoked ring response signal.

5. The method of claim 4, wherein measuring the delay interval comprises measuring a time difference between the bipolar stimulation pulse and any one of:
    an onset of the unipolar evoked ring response signal;
    a peak amplitude of the unipolar evoked ring response signal; and
    a peak slope of the unipolar evoked ring response signal.

6. The method of claim 4, wherein detecting anodal stimulation comprises ignoring a detected stimulation if a delay is measured between the bipolar stimulation pulse and the unipolar evoked ring response signal characteristic.

7. The method of claim 6, further including the steps of performing automatic capture verification, and setting a stimulation output setting equal to a bipolar capture threshold plus a working margin.

8. The method of claim 4, wherein detecting anodal stimulation comprises accounting for a detected stimulation if no delay is measured between the bipolar stimulation pulse and the unipolar evoked ring response signal characteristic.

9. The method of claim 8, wherein, if anodal stimulation is detected, omitting automatic capture verification.

10. The method of claim 8, wherein, if anodal stimulation is detected, performing a capture threshold search.

11. The method of claim 1, wherein performing the capture threshold search comprises performing an anodal stimulation threshold test on a periodic basis.

12. The method of claim 11, wherein performing the anodal stimulation threshold test comprises:
    delivering a bipolar stimulation pulse at a number of output settings;
    detecting if anodal stimulation occurs following each bipolar stimulation pulse; and
    setting a lowest bipolar stimulation output at which anodal stimulation is detected as the anodal stimulation threshold.

13. The method of claim 12, further including comparing the anodal stimulation threshold to a previously measured anodal stimulation threshold.

14. The method of claim 13, further including performing a capture threshold search if an anodal stimulation threshold is different than a previously measured anodal stimulation threshold.

15. The method of claim 14, further including the steps of performing a capture threshold search, and automatically adjusting a stimulation output, upon detection of a decrease in the anodal stimulation threshold.

16. The method of claim 14, further including the steps of performing a capture threshold search, and automatically adjusting a stimulation output, upon detection of an increase in the anodal stimulation threshold above a predetermined value.

17. A cardiac stimulation device that performs automatic capture verification during bipolar stimulation, comprising:

a pulse generator that selectively generates stimulation pulses;

a detector that monitors for anodal stimulation during bipolar stimulation; and a controller, connected to the pulse generator, that ignores a detected response for purposes of capture verification if anodal stimulation is detected, and that performs capture verification based on the detected response if anodal stimulation is not detected.

18. The device of claim 17, further including an electrode that functions as an anode during bipolar stimulation; and a sensor, connected to the electrode, to sense a unipolar evoked ring response signal.

19. The device of claim 18, further including a timing circuit that sets an evoked response detection window following the delivery of a bipolar stimulation pulse.

20. The device of claim 19, wherein the timing circuit measures a delay interval between a bipolar stimulation pulse and a predefined characteristic of a unipolar evoked ring response signal.

21. The device of claim 20, wherein the predefined characteristic of the unipolar evoked ring response signal comprises any one of:

an onset of the unipolar evoked ring response signal;

a peak amplitude of the unipolar evoked ring response signal; and a peak slope of the unipolar evoked ring response signal.

22. A cardiac stimulation device that performs automatic capture verification during bipolar stimulation, the device comprising:

means for detecting anodal stimulation during bipolar stimulation;

means for rejecting a detected response if anodal stimulation is detected; and means for performing capture verification on the detected response if anodal stimulation is not detected.

23. The device of claim 22, wherein the means for detecting anodal stimulation comprises means for sensing a unipolar evoked ring response signal from an electrode functioning as an anode during bipolar stimulation.

24. The device of claim 23, further comprising:

means for setting an evoked response detection window following the delivery of a bipolar stimulation pulse;

means for sampling the unipolar evoked ring response signal during the evoked response detection window; and means for measuring a delay interval between a bipolar stimulation pulse and a predefined characteristic of a unipolar evoked ring response signal.

25. The device of claim 24, wherein the means for measuring the delay interval comprises means for measuring a time differential between the bipolar stimulation pulse and any one of:

an onset of the unipolar evoked ring response signal;

a peak amplitude of the unipolar evoked ring response signal; and a peak slope of the unipolar evoked ring response signal.

26. The device of claim 24, wherein the means for detecting anodal stimulation ignores a detected stimulation if a delay is measured between the bipolar stimulation pulse and the unipolar evoked ring response signal characteristic.

27. The device of claim 26, further including means for performing automatic capture verification, and means for setting a stimulation output setting equal to a bipolar capture threshold plus a working margin.

28. The device of claim 24, wherein the means for detecting anodal stimulation comprises means for accounting for a detected stimulation if no delay is measured between the bipolar stimulation pulse and the unipolar evoked ring response signal characteristic.

29. The device of claim 28, wherein the means for verifying capture does not perform capture verification if anodal stimulation is detected.

30. The device of claim 29, further including means for performing a capture threshold search if anodal stimulation is detected.

31. In an implantable cardiac stimulation device, a method of determining whether an operating mode comprising capture verification combined with bipolar stimulation is warranted, wherein the implantable cardiac stimulation device includes a lead having at least two electrodes capable of bipolar stimulation, the method comprising:

delivering a bipolar stimulation pulse to a chamber of the heart;

monitoring for anodal stimulation on a first one of the electrodes following delivery of the stimulation pulse;

determining that the operating mode is not warranted if anodal stimulation is detected on the first electrode; and determining that the operating mode is warranted if anodal stimulation is not detected on the first electrode.

* * * * *